United States Patent [19]

Margolskee

[11] Patent Number: 5,270,185
[45] Date of Patent: Dec. 14, 1993

[54] HIGH-EFFICIENCY CLONING OF CDNA

[75] Inventor: Robert F. Margolskee, Upper Montclair, N.J.

[73] Assignee: Hoffmann-La Roche Inc., Nutley, N.J.

[21] Appl. No.: 928,856

[22] Filed: Aug. 12, 1992

Related U.S. Application Data

[63] Continuation of Ser. No. 341,523, Apr. 21, 1989, abandoned.

[51] Int. Cl.$^5$ .................... C12N 15/10; C12N 15/64
[52] U.S. Cl. ........................ 435/91.41; 435/172.3; 435/320.1
[58] Field of Search ............. 435/320.1, 91, 172.3; 536/27; 935/8.7, 18.23, 52.80

[56] References Cited

U.S. PATENT DOCUMENTS

4,985,359 1/1991 Oberbaumer ................. 435/91

OTHER PUBLICATIONS

Bower et al. (1987), Nucleic Acid Research, vol. 15, pp. 3531-3533.
Current Protocols (1987), pp. 3.6.1-3.6.2.
Han et al. (1987), Biochemistry, vol. 26, pp. 1617-1625.
Deininger (1987), Methods in Methodology, vol. 152, pp. 371-389.
BRL Catlog (1988) p. 95.
Okayama, et al., Mol. Cell Biol. 2:161 (1982).
Okayama, et al., Mol. Cell Biol. 3:280 (1983).
Okayama, et al., Methods in Enzymology 154:3 (1987).
Margolskee, et al., Mol. Cell Biol. 8:2837 (1988).
Gubler, et al., Gene 25:263 (1983).
Kimmel, et al., Methods in Enzymology 152:307 (1987).
Dower, et al., Nucleic Acids Res. 13:6127 (1988).
Yanisch-Perron, et al., Gene 33:103 (1985).
Bottger, BioTechniques 6:878 (1988).
Aruffo, et al., Proc. Natl. Acad. Sci. USA 84:8573 (1987).
Huynh et al., DNA Cloning, A Practical Approach, vol. 1, Chapter 2 (IRL Press, Glover ed., 1985).
Sorge, Strategies in Molecular Biology 1:3 (1988).

*Primary Examiner*—Richard A. Schwartz
*Assistant Examiner*—Kathleen L. Choi
*Attorney, Agent, or Firm*—George M. Gould; William H. Epstein; Patricia S. Rocha

[57] ABSTRACT

Asymmetrically tailed plasmid primers are provided, each of which comprises a cut, double-stranded DNA plasmid containing a functional origin of replication, at least one functional selection marker gene, a 3' oligo (dT) tail and a 3' oligo (dC) or oligo (dG) tail which is terminated by a phosphate group. Methods for making and using the primers for the highly efficient production of complex cloning libraries and a kit for carrying out the cloning method of the invention are also provided.

20 Claims, 4 Drawing Sheets

```
         Sac 1      Not 1
    5'pCCCCCGGGGCCGCCGCCCCCCCCp3'
    3'TCGAGGGGCCGGCGGCGGGp 5'
```

FIG. 3A

```
         Kpn 1      Not 1
    5' pCGGGGGCCGGGCCGC(T) 3'
                              40
    3' CATGGCCCCGCCGGGCp5'
```

```
         Eco R1     Not 1
    5'pAATTCCCCGGGGCCGCCCCCCCCCp3'
    3'GGGGCCGGCGGGCp5'
```

FIG. 3B

```
         Hin dIII   Not 1
    5'pAGCTTGGGGGCCGGGCCGC(T) 3'
                                 40
    3'ACCCCGCCGGGCCGGCGp5'
```

HIGH-EFFICIENCY CLONING OF CDNA

This is a continuation of application Ser. No. 07/341,523, filed Apr. 21, 1989, now abandoned.

TECHNICAL FIELD

This invention relates to novel asymmetrically tailed plasmid primers and to methods for making and using such primers for the highly efficient cloning of cDNA.

BACKGROUND OF THE INVENTION

Rapid developments in the field of recombinant DNA technology in recent years have made it possible to produce a wide range of biologically important polypeptides and proteins in high yields. Essential to such production is the availability of DNA sequences coding for the desired products. Generally, such DNA sequences are produced enzymatically using populations of messenger RNA (mRNA) isolated from cells known to produce the desired polypeptide or protein as templates. Complementary DNA strands are first produced from the mRNA templates, and second DNA strands are then produced using the first DNA strands as templates.

The result is a mixture of duplex complementary DNA (cDNA) molecules which together comprise a cDNA "library". The cDNAs in such libraries can be replicated through cloning in appropriate host cells and identified by the use of molecular probes, antibodies or biological activity assays.

A number of scientific investigators have devised methods for producing cDNA libraries. One widely used method is that of Okayama et al. [Mol. Cell. Biol. 2:161 (1982)]. This method employs an oligo (dT)-tailed plasmid primer and an oligo (dG)-tailed linker DNA. Applying the method to rabbit reticulocyte mRNA, Okayama et al. produced about $10^5$ globin cDNA clones per $\mu$g of mRNA. More recently, using highly competent cells, the Okayama et al. method has been found to yield 1 to $2 \times 10^6$ clones per $\mu$g of plasmid vector [Okayama et al., Meth. Enzymol. 154:3 (1987); Margolskee et al., Mol. Cell. Biol. 8:2837 (1988)]. Gubler et al. [Gene 25:263 (1983)] reported a method for generating cDNA libraries which avoids the use of plasmid primers and produces a cloning efficiency of as high as $10^6$ recombinants per $\mu$g of mRNA. These and other cDNA cloning methods have been reviewed by Kimmel et al. [Meth. Enzymol. 152:307 (1987)].

Although the foregoing methods have been used to make cDNAs coding for a variety of polypeptides and proteins, the efficiency of such methods may be inadequate if a desired mRNA species is present in relatively low abundance in the total isolated mRNA population. For the cloning of such minor species, substantially higher cloning efficiencies are required.

SUMMARY OF THE INVENTION

This invention provides asymmetrically tailed plasmid primers, each of which comprises a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group.

This invention further provides a method for making an asymmetrically tailed plasmid primer, comprising:

(a) cleaving a double-stranded DNA plasmid containing a functional origin of replication and at least one functional selection marker gene at two unique restriction endonuclease sites, which cleavage leaves intact the origin of replication and the selection marker gene and produces two different cut ends;

(b) ligating a first double-stranded oligonucleotide adaptor to one of the cut ends of the plasmid, one end of which adaptor is complementary to the cut end of the plasmid, the other end of which adaptor contains an oligo (dT) extension; and (c) ligating a second double-stranded oligonucleotide adaptor to the other cut end of the plasmid, one end of which adaptor is complementary to the cut end of the plasmid, the other end of which adaptor contains an oligo (dC) or oligo (dG) extension terminated by a 3' phosphate group.

The order of ligating the adaptors can be reversed, or the ligation of both adaptors can be carried out simultaneously.

This invention still further provides a method for the cloning of cDNA, comprising:

(a) providing an asymmetrically tailed plasmid primer comprising a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group;

(b) treating a mRNA preparation with the primer under conditions in which polyadenylate tails in the mRNA specifically anneal to the oligo (dT) extension of the primer to form a primer:mRNA complex;

(c) treating the primer:mRNA complex under conditions in which a first cDNA strand is synthesized using the annealed mRNA as a template, thereby forming a primer-linked cDNA:mRNA duplex;

(d) adding an oligo (dG) or oligo (dC) extension to the 3' end of the first cDNA strand, which extension is complementary to the phosphate-terminated extension of the primer; and (e) treating the cDNA:mRNA duplex of step (d) under conditions in which a second cDNA strand is synthesized, using the first cDNA strand as a template.

In a preferred embodiment of the invention, cDNA is cloned by a method comprising:

(a) providing an asymmetrically tailed plasmid primer comprising a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group;

(b) treating a mRNA preparation with the primer under conditions in which polyadenylate tails in the mRNA specifically anneal to the oligo (dT) extension of the primer to form a primer:mRNA complex;

(c) treating the primer:mRNA complex under conditions in which a first cDNA strand is synthesized using the annealed mRNA as a template, thereby forming a primer-linked cDNA:mRNA duplex;

(d) adding an oligo (dG) or oligo (dC) extension to the 3' end of the first cDNA strand, which extension is complementary to the phosphate-terminated extension of the primer;

(e) annealing the oligo (dG) or oligo (dC) extension of the first cDNA strand to the phosphate-terminated extension of the primer;

(f) ligating the 3' terminus of the oligo (dG) or oligo (dC) extension to the 5' end of the primer;

(g) removing the 3' phosphate group from the phosphate-terminated extension of the primer;

(h) digesting the mRNA in the cDNA:mRNA duplex;

(i) synthesizing a second cDNA strand using the first strand as a template;

(j) ligating the second cDNA strand to the plasmid to form a closed circular plasmid;

(k) introducing the closed circular plasmid into a unicellular host organism; and (l) culturing the host organism under conditions in which the plasmid is replicated.

Figure 1:
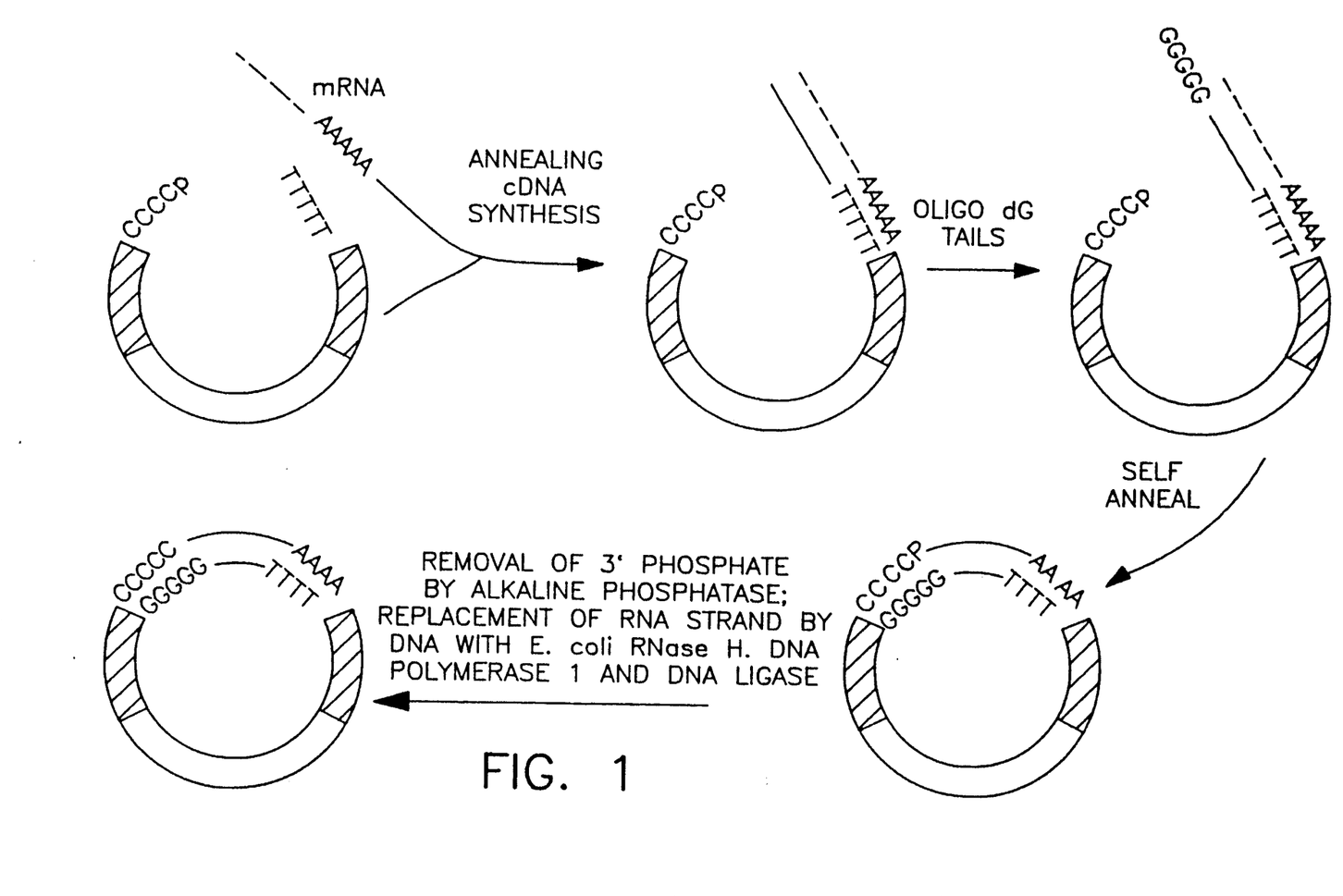
FIG. 1 is a schematic representation of one method by which an asymmetrically tailed plasmid primer of the invention is used to clone cDNA.

The method of this invention, which is illustrated schematically in FIG. 1, is superior to the methods of the prior art because it is simpler and faster and produces cDNA libraries that are much more complex (i.e., the method produces a larger number of cDNAs and cDNA from less abundant mRNA species). While the method of Okayama et al., supra, takes 4 days to complete, for example, the method of this invention can be carried out in half that time. The complexities of the libraries produced according to this invention are about 15-fold greater than the best results that can otherwise be obtained.

BRIEF DESCRIPTION OF THE FIGURES

This invention can be more readily understood by reference to the accompanying figures, in which

FIG. 3 shows the nucleotide sequences of pairs of oligonucleotide adaptors that can be used to make plasmid primers of the invention beginning with plasmid pLP (FIG. 3A) and with plasmid pUC19 (FIG. 3B)

DESCRIPTION OF THE INVENTION

Many standard methods known in the art and useful in this invention have been described by Maniatis et al., Molecular Cloning: A Laboratory Manual, Cold Spring Harbor Laboratory, 1982. This reference and all other references cited herein are hereby incorporated in their entirety by reference.

The novel asymmetrically tailed plasmid primers of the invention all contain one 3' terminal oligo (dT) extension and one 3' terminal oligo (dC) or oligo (dG) extension. The latter extension is terminated by a 3' phosphate group. This configuration allows one to prime first-strand cDNA synthesis at the dT end, tail the cDNA with deoxyguanylate (dG) or deoxycytidylate (dC) residues, self-anneal the plasmid-primed cDNA to the complementary extension of the plasmid, remove the 3' phosphate block and complete the synthesis of a double-stranded cDNA, all in a single plasmid primer. The presence of the 3' phosphate group in the primers ensures that dG or dC residues will not be added to the oligo (dC) or oligo (dG) extensions of the primers during dG or dC tailing of the first cDNA strand.

As used above, the term "complementary extension" means that if the phosphate blocked extension of the primer contains deoxyguanylate residues, the tail added to the first cDNA strand will contain deoxycytidylate residues, and vice versa.

The lengths of the oligo (dT) extensions should range from about 10 to about 200 residues, although more residues could be used. A length of from about 40 to about 60 deoxythymidine residues is preferred. Lengths of the oligo (dC) or oligo (dG) extensions can range from about 8 to about 25 residues, although a range of from about 10 to about 12 residues is preferable.

Such asymmetrically tailed plasmid primers are made by cleaving one of any number of available Cloning plasmids and then modifying the cut ends of such plasmids with appropriate oligonucleotide adaptor molecules. All that is required is that a given starting plasmid contain two unique restriction sites, the cleavage of which by the corresponding restriction enzymes will not destroy the origin of replication of the plasmid and will preserve at least one marker for selection in an appropriate host cell, such as ampicillin or tetracycline resistance.

A starting plasmid selected for use in this invention will have two unique restriction sites, and cleavage at the restriction sites will preferably produce two different overhanging (sticky) termini. This is desirable because annealing and ligation of two different oligonucleotide adaptors to produce the plasmid primers of the invention is easier with such termini.

Figure 2:
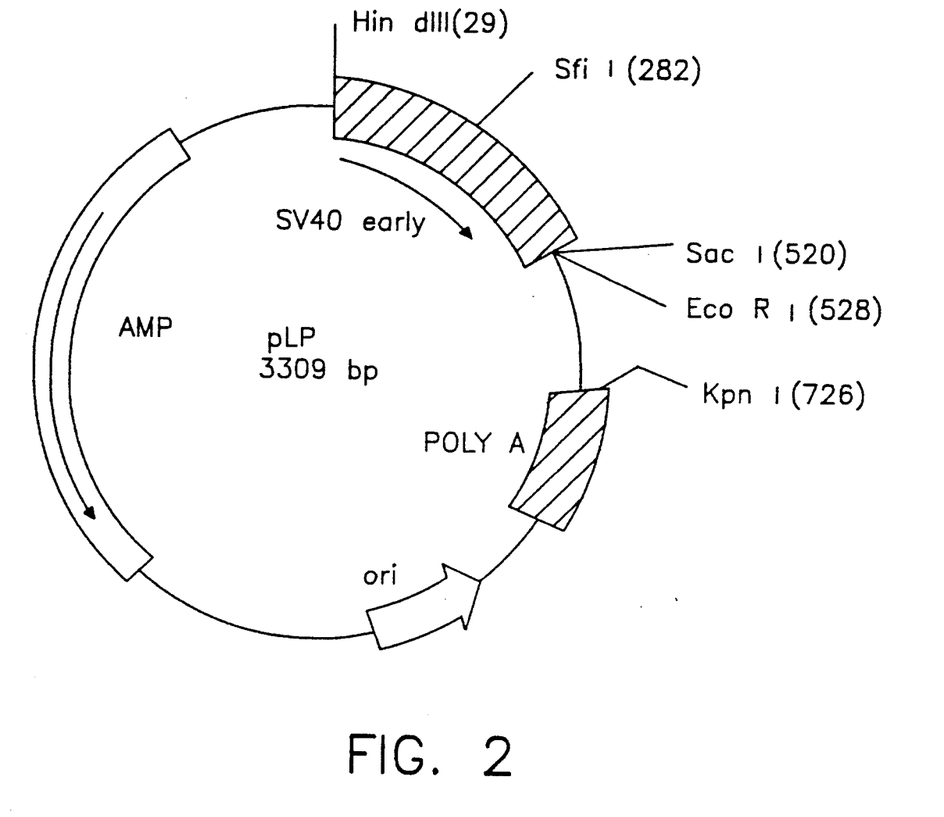
FIG. 2 is a schematic representation of exemplary plasmid pLP.
Figure 3A:
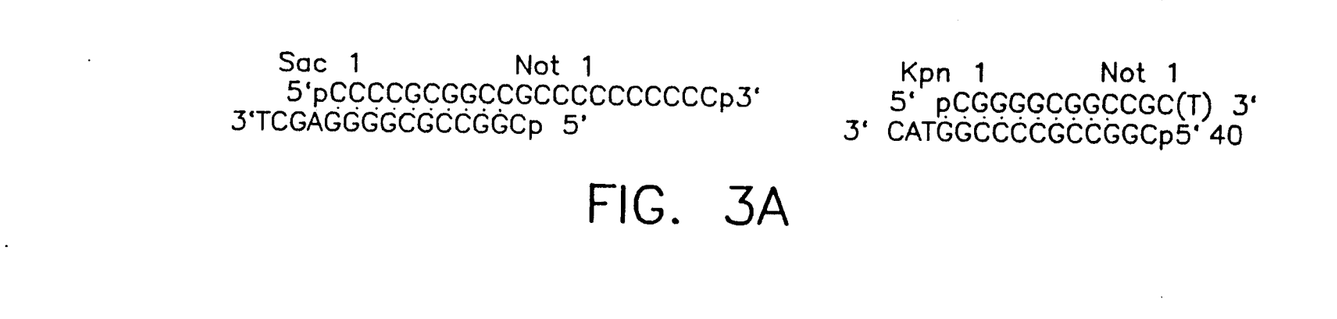
Figure 4:
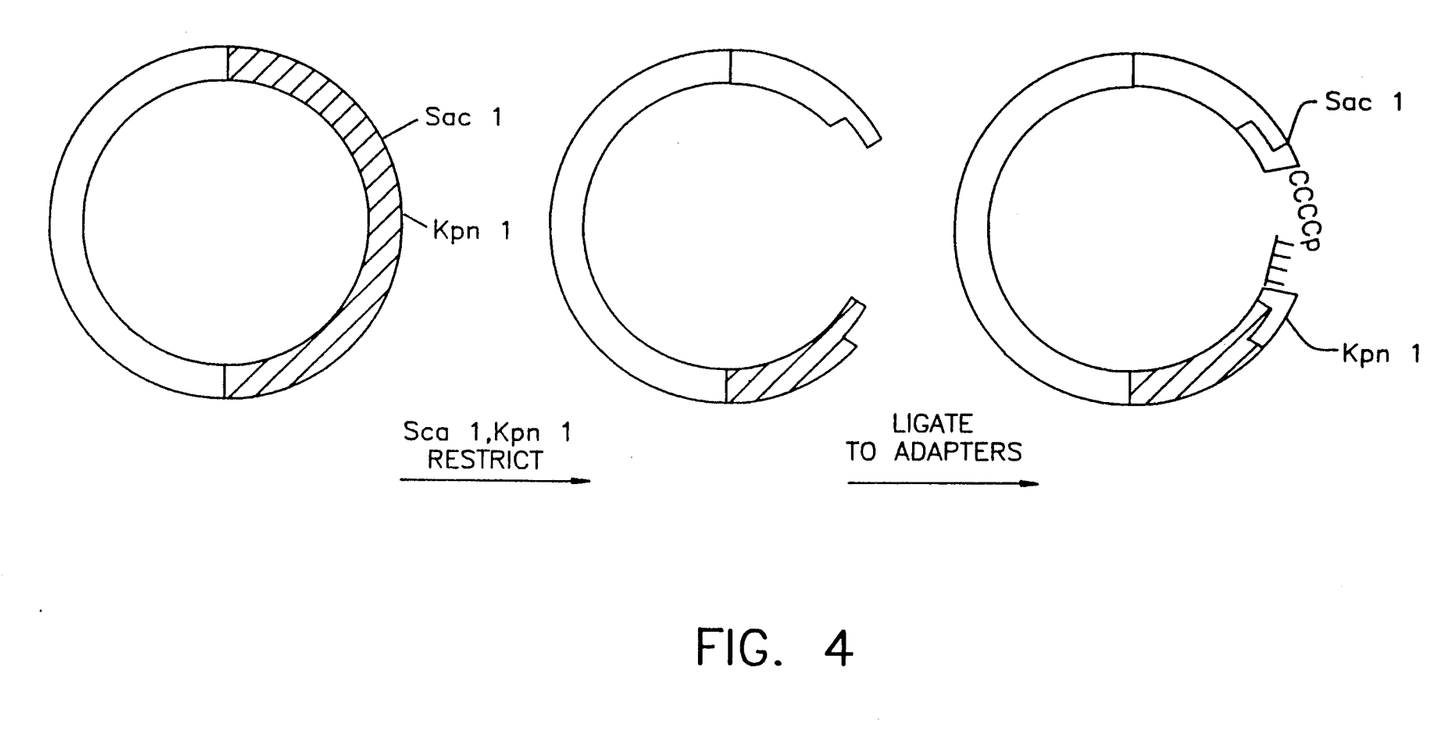
FIG. 4 is a schematic representation showing how plasmid pLP was modified by restriction endonuclease cleavage and adaptor ligation to produce a representative asymmetrically tailed plasmid primer of the invention.

To illustrate this invention, the cleavage and asymmetric tailing of a plasmid designated pLP (FIG. 2) is described in the Example below. Because pLP contains unique Sac I and Kpn I restriction sites that are positioned so as to meet the requirement that the origin of replication and at least one selection marker gene be preserved following cleavage, cleavage at these sites was carried out. As a result, oligonucleotide adaptors were used which were complementary to the nucleotide sequences at the restriction sites and which also contained the necessary oligo (dT) and 3' phosphate-blocked oligo (dC) extension sequences (FIG. 3A). The construction of a representative plasmid primer of this invention using plasmid pLP and such adaptors is shown schematically in FIG. 4.

Since the sequences of numerous other restriction sites are well known in the art, complementary oligonucleotide adaptors can readily be made to fit overlapping termini produced by cleavage at other unique sites in a wide variety of other plasmids.

Figure 3B:
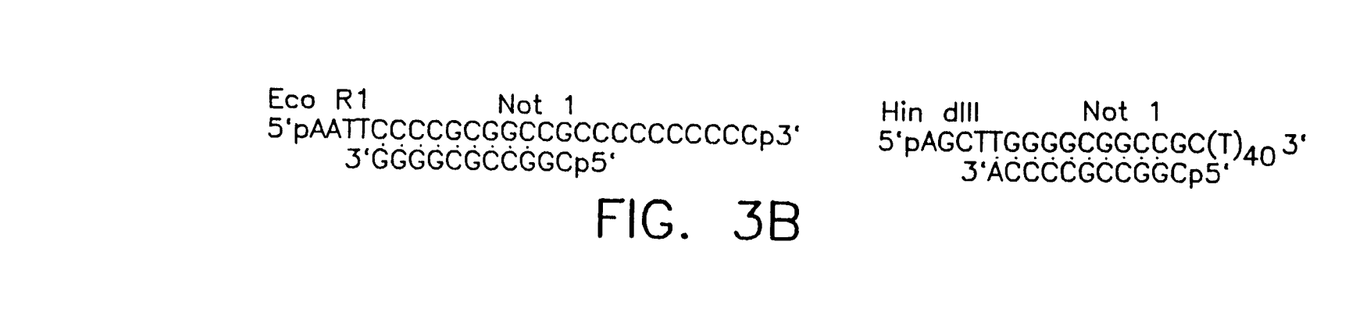

For example, the commercially available plasmid pUC19 can readily be modified to make a plasmid primer of this invention. pUC19 contains unique Eco RI and Hin dIII sites in the polylinker region that can be used. Following double cleavage at these sites, adaptors shown in FIG. 3B can be ligated to the cut plasmid by analogy to the construction of the pLP-derived asymmetrically tailed plasmid primer.

Preferably, a plasmid selected for use in this invention will also be capable of directing the expression of the cloned DNA in a host cell. Tailed plasmid pLP, for example, is capable of directing expression of the DNA in mammalian cells such CHO or COS cells.

Adaptors prepared to fit a given cut plasmid may also be used for plasmids which must be cleaved with other restriction enzymes. In such cases, the termini produced by cleavage must be modified by ligation of appropriate oligonucleotides, to generate the restriction sites for which the adaptors were designed. Such modification can readily be carried out using standard methods well known in the art.

Although starting plasmids which yield two different overhanging termini upon cleavage are preferred, the plasmid primers of this invention can also be produced if cleavage instead produces one blunt end and one overhanging end. In that case, one end of the adaptor ligated to the blunt end of the cut plasmid will have a blunt end, while the other end of this adaptor will contain an oligo (dT) or a 3' phosphate-blocked oligo (dC) or oligo (dG) extension.

Oligonucleotide adaptors used in the construction of the asymmetrically tailed plasmid primers of the invention are double-stranded DNA molecules comprising two single-stranded DNA molecules which are annealed together to produce a duplex (FIG. 3). One end of this duplex is complementary to one end of the cleaved plasmid; the other end of the duplex contains an oligo (dT) or a 3' phosphate-blocked oligo (dC) or oligo (dG) extension.

The nucleotide sequences in the strands between the termini of the adaptors, which can contain from about 8 to 100 or more nucleotide residues, are complementary and serve to bond the single strands comprising the duplexes together by hydrogen bonding. If desired, the nucleotide sequences between the termini can comprise one or more restriction cleavage sites not otherwise present in the plasmid, which can be used to excise the desired cDNA from the plasmid after cloning by the method of this invention has been completed.

Oligonucleotides used in the adaptors of the invention which do not contain a 3' phosphate group can readily be chemically synthesized using standard methods well known in the art. See, e.g., Narang et al., Meth. Enzymol. 68:90 (1979) (phosphotriester method); Brown et al., Meth. Enzymol. 68:109 (1979) (phosphodiester method). Oligonucleotides used in the adaptors which do contain a 3' phosphate group can be obtained custom-synthesized from commercial sources such as the Midland certified Reagent Co., Midland, Tex.

Messenger RNA from any source can be cloned by the method of this invention, including bacteria, yeast and higher organisms such as plants or animals. Preferably, the source selected will be one that is known to produce the desired product in substantial amounts. Because of the high efficiency of the method, however, sources producing only minor amounts of the desired mRNA can also be used. Furthermore, minute (submicrogram) amounts of mRNA can be used to generate high-complexity cDNA libraries by this method.

Once cloning is completed according to the invention, the desired clone(s) can be detected by using polyclonal or monoclonal antibodies prepared against the product in a conventional immunoassay, a labeled probe or an appropriate bioassay.

In the method of the invention, necessary ligation steps are carried out using an enzyme such as E. coli or T4 DNA ligase in the presence of $Mg^{++}$ and nicotinamide adenine dinucleotide or adenosinetriphosphate (ATP), as described, e.g., by Maniatis et al., supra at page 146.

Annealing of mRNA to the primers of the invention is generally carried out using a molar excess of RNA of about 3:1 (mRNA:primer), where the quantity of mRNA is known. If the amount of mRNA is not known, small quantities of the primers should be used to ensure that a large excess of mRNA is present. Annealing is carried out during the first-strand reaction at a temperature of from about 37 to about 42° C. for a period of from about 30 to 60 minutes.

First-strand cDNA synthesis is carried out using the annealed mRNA as a template in the presence of adequate amounts of the deoxyribonucleoside triphosphates dATP, dCTP, dGTP and TTP, $Mg^{++}$ and a reverse transcriptase such as Moloney murine leukemia virus or avian myeloblastosis virus reverse transcriptase. Upon completion of the synthesis of the first strand and removal of unincorporated dXTPs (e.g., by gel filtration or differential precipitation), the 3' end of the cDNA first strand is tailed with oligo (dG) or oligo (dC) using terminal deoxynucleotidyl transferase in the presence of $Co^{++}$ and dGTP or dCTP. The presence of the 3' phosphate block in the oligo (dC) or oligo (dG) extensions of the plasmids ensures that the tailing with the complementary bases will occur only at the terminus of the first cDNA strand.

Cyclization of the plasmids is achieved by self-annealing of the oligo (dC) and (dG) tails at a temperature of from about 35 to about 50° C. for a period of from about 30 to about 120 minutes, followed by ligation. Following this ligation, the 3' phosphate block is removed by treatment with alkaline phosphatase.

Replacement of the RNA with second-strand cDNA can be carried out essentially as described by Okayama et al. [Mol. Cell. Biol. 2:161 (1982); Mol Cell. Biol. 3:280 (1983)]. This process entails digestion of the RNA with a ribonuclease such as E. coli RNase H, repair synthesis using a DNA polymerase having the activities of DNA polymerase I, and ligation.

When second-strand synthesis follows limited (nick) digestion of the RNA with RNase H, the DNA polymerase used should have both 5' exonuclease activity and synthetic activity, like DNA polymerase I. Another example of such an enzyme is the DNA polymerase of M. luteus. In such cases, the partially digested mRNA may act as a primer, although whether or not it does is not essential to the invention. If, instead, the RNA is exhaustively digested with RNase H or removed by hydrolysis with alkali, other DNA polymerases which lack 5' exonuclease activity such as T4 DNA polymerase or the Klenow fragment of DNA polymerase I can be used for the second-strand synthesis.

The closed circular plasmids can be introduced into a compatible unicellular host organism. Although any of the standard transformation protocols known in the art can be used [see, e.g., Higa et al., J. Mol. Biol. 53:159 (1970); Miller, in Guide to Molecular Cloning Techniques, 1987, Berger et al. (Eds), Academic Press, New York, pp. 145-173], the electro-transformation method of Dower et al. [Nucleic Acids Res. 13:6127 (1988)] is preferred. Transformants are selected by culturing in the presence of an agent, resistance to which is provided by the plasmid primer used.

Reverse transcriptase also possesses an RNase H activity. Therefore, it may be possible to carry out the method of this invention without separately adding the latter enzyme.

Because *E. coli* bacteria contain RNase H, DNA polymerase I, a DNA ligase and phosphatase activity, it should be possible to complete the method of the invention by introducing the asymmetrically tailed plasmid primers into *E. coli* after first-strand cDNA synthesis and the tailing thereof have been completed. This can be done either before or after ligation of the tailed first strand has been carried out.

It will be apparent to those skilled in the art that order of some of the individual steps of the preferred cloning method embodiment can be varied, although there may be some reduction in cloning efficiency if this is done. For example, the phosphate block can instead be removed prior to ligation of the 3' terminus of the tailed first cDNA strand to the 5' end of the primer. It is also possible to delete removal of the phosphate block altogether. Any and all such variations are within the scope of the invention.

For convenient use in carrying out the cloning of mRNA by the method of this invention, a kit can be prepared comprising one bottle each of solutions containing the following reagents in quantities sufficient to carry out multiple clonings:

(a) an asymmetrically tailed plasmid primer comprising a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group;
(b) a DNA ligase;
(c) a terminal deoxynucleotidyl transferase;
(d) a reverse transcriptase;
(e) a DNA polymerase;
(f) a ribonuclease;
(g) an alkaline phosphatase; and
(h) a host unicellular organism.

In addition to the plasmid primers described above, this invention also provides asymmetrically tailed plasmid primers, each of which comprises a double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' ribonucleotide group. Like a phosphate group, a ribonucleotide group at the 3' terminus prevents undesired tailing of the plasmid, during tailing of the first cDNA strand.

The methods for making and using such primers and kits containing them are analogous to the foregoing methods and kits employing asymmetrically tailed phosphate-blocked plasmid primers, with one exception. An alkaline phosphatase is not required during the cloning of cDNA to remove such blocking groups. Instead, they are readily removed by a DNA polymerase having 3' exonuclease activity like DNA polymerase I.

Any ribonucleotide can be used as a 3' block in this invention (e.g., an adenylate, guanylate, uridylate or cytidylate group). Oligonucleotides containing 3' ribonucleotide groups needed to make the adaptors of the invention can be obtained custom-synthesized from commercial sources such as the Midland Certified Reagent Co., Midland, Tex.

EXAMPLE

The preparation and use of a representative plasmid primer of this invention were carried out as described below.

Enzymes and Chemicals

Enzymes and chemicals were purchased from the following suppliers: Avian Myeloblastosis Virus reverse transcriptase, Seikagaku America, Inc., St. Petersburgh, Fla.; oligo $dT_{12}$, RNase H, terminal deoxynucleotidyl transferase, *E. coli* ligase, Pharmacia-LKB Biotechnology Inc., Piscataway, N.J.; calf intestine alkaline phosphatase, Asp 718, DNA polymerase I, Boehringer Mannheim Biochemicals, Indianapolis, Ind.; Klenow Fragment, Bethesda Research Laboratories, Bethesda, Md.; Hin dIII, Pst I, Acc I, Eco RI, Sac I, Kpn I, T4 DNA ligase, polynucleotide kinase, T4 DNA polymerase, New England Biolabs, Inc., Beverly, Mass. Restriction endonuclease buffers were as recommended by the manufacturers.

Enzyme units were as defined by the manufacturers. Reverse transcriptase (10 units/$\mu$l): one unit incorporates one nanomole of dTMP into acid-insoluble product in 10 minutes at 35° C. RNase H (800 units/ml): one unit produces 1 nanomole of acid-soluble nucleotide in 20 minutes at 37° C. Terminal deoxynucleotidyl transferase (20 units/$\mu$l): one unit transfers 1 nanomole of dAMP to $p(dT)_6$ per hour at 37° C. *E. coli* ligase (0.25 mg protein/ml). Alkaline phosphatase (1 unit/$\mu$l): one unit hydrolyses 1 $\mu$mol of p-nitrophenyl phosphate in 1 minute at 37° C. DNA polymerase I (5 units/$\mu$l): one unit incorporates 10 nmol of total nucleotide into an acid-precipitable fraction in 30 minutes. Klenow fragment (6 units/$\mu$l): one unit incorporates 10 nmol of total deoxyribonucleotides into an acid-insoluble form in 30 minutes at 37° C. T4 DNA ligase (400 units/$\mu$l): one unit gives 50% ligation of Hin dIII-digested $\lambda$ DNA in 30 minutes at 16° C. Polynucleotide kinase (10 units/$\mu$l): one unit produces 1 nmole of acid-insoluble material in 30 minutes at 37° C. T4 DNA polymerase (1 unit/$\mu$l): one unit incorporates 10 nmoles of dNTP into acid-precipitable material in 30 minutes at 37° C. All restriction endonuclease units are defined as the amount of enzyme required to produce a complete digest of 1 $\mu$g DNA in 60 minutes.

DNA Preparation

Small scale isolation of plasmid ("mini-prep") DNA from saturated overnight cultures was carried out according to the method of Holmes et al. [Anal. Biochem. 114:193 (1981)] as modified by Margolskee et al. [Mol. Cell. Biol. 8:2837 (1988)]. This procedure allows one to obtain small amounts of DNA (about 1 to 5 $\mu$g) from a 1 ml culture of *E. coli* for analytic purposes and for construction of modified vectors. Large scale preparation of plasmid DNA employed chloramphenical amplification of late log phase cultures, followed by alkaline lysis harvesting and purification by two cycles of equilibrium centrifugation in cesium chloride-ethidium bromide gradients as described by Maniatis et al. (supra, pp. 88–94).

Specific restriction fragments were purified by preparative electrophoresis in 1% agarose (Seaplaque, FMC Inc., Rockland, Me). Twenty×13-$\frac{1}{2}$ cm gels were run at 36 to 100 volts overnight (15 to 20 hours) in Tris-Borate-EDTA buffer containing 0.5 $\mu$g/ml of ethidium bromide (Maniatis et al., supra, at p. 454).

DNA was visualized with long-wave UV transillumination, the bands of interest were excised, and the DNA was recovered from gels by electroelution utilizing an electrophoretic sample concentrator (ISCO, Inc., Lincoln, Nebr). Electroeluted DNA was extracted with phenol-chloroform, then chloroform, followed by ethanol precipitation at −20° C. for at least 4 hours.

Construction of Plasmids

Plasmid pLP was derived from plasmids pL, pcDV and pUC19 as described below. Plasmids pL and pcDV are available from Pharmacia LKB, Piscataway, N.J. Plasmid pUC19 can be purchased from Bethesda Research Laboratories, Bethesda, Md.

(1) pUCL1. Plasmid pUCL1 contains the SV40 regulatory region from plasmid pL [Okayama et al., Mol. Cell. Biol. 3:280 (1983)] cloned between the Hin dIII and Pst I sites within the polylinker region of plasmid pUCDPK (see below). Five μg of pL DNA was digested with restriction endonucleases Hin dIII (20 units) and Pst I (20 units) for 2½ hours at 37° C. in Pst I buffer [100 mM NaCl, 20 mM Tris-HCl (pH 7.5), 10 mM MgCl$_2$, 100 μl/ml BSA (bovine serum albumin)] in a volume of 60 μL. The 520 bp Hin dIII-Pst I fragment from pL was isolated by gel electrophoresis and electroelution. One μg of pUCDPK (construction described below) miniprep DNA was digested with restriction endonucleases Hin dIII (50 units) and Pst I (50 units) for 3 hours at 37° C. in buffer in a volume of 100 μl. Subsequently, 5 μl of 1M glycine (pH 9.4) and 0.5 μl (0.5 units) calf intestine alkaline phosphatase (CIAP) were added to the reaction, which was then incubated at 37° C. for 20 minutes. The restricted, phosphatased pUCDPK vector was isolated by preparative gel electrophoresis and electroelution. Ligation of electroeluted pUCDPK (3.5 ng) to the 520 bp piece of pL (1 ng) was carried out overnight at 12° C. in the presence of T4 DNA ligase (80 units) in a volume of 10 μl, in T4 DNA ligation buffer [50 mM Tris-HCl (pH 7.8), 10 mM, MgCl$_2$, 20 mM DTT, 1 mM ATP, 50 μg/ml BSA]. The ligation mixture was used to directly transform E. coli DH1 (Bethesda Research Laboratories, Bethesda, Md.) according to the vendor's instructions. Transformants were plated out on Luria Broth (LB) ampicillin (50 μg/ml) agar plates. Mini-prep DNAs from ampicillin resistant colonies were screened by cleavage with Pst I and Hin dIII followed by analysis on 1% agarose gel. An isolated clone (pUCL1) with Pst I - Hin dIII fragments from both pL and pUCDPK was grown up by the large-scale plasmid procedure.

(2) pUCDPK. Plasmid pUCDPK was derived from plasmid pUC19 [Yanisch-Perron et al., Gene 33:103 (1985)]. One μg of pUC19 DNA was digested with restriction endonucleases Acc I (8 units) and Asp 718 (18 units) for 4 hours at 37° C. in Sfi I buffer [50 mM NaCl, 10 mM Tris-HCl (pH 7.8), 20 mM MgCl$_2$, 20 mM 2-mercaptoethanol, 100 μg/ml BSA] in a volume of 50 μl. All four deoxynucleotide triphosphates were added (166 μmolar, final concentration), and the Klenow fragment of DNA polymerase (3 units) was used to fill in the ends of the DNA by incubation for 30 minutes at room temperature. Five minutes at 70° C. inactivated the Klenow fragment. A portion of the blunt ended material (185 ng) was self-ligated at 12° C. overnight by T4 DNA ligase (600 units) in a 50 μl reaction containing T4 DNA ligase buffer. This ligation product was treated with Bam HI (50 units) for 20 minutes at 37° C. in Bam HI buffer [150 mM NaCl, 6 mM Tris-HCl (pH 7.9), 6 mM MgCl$_2$, 6 mM 2-mercaptoethanol, 100 μg/ml BSA]. This material was used to directly transform E. coli DH1; transformants were plated out on LB ampicillin plates. Mini-prep DNAs from ampicillin resistant colonies were screened by cleavage with Asp 718, Acc I and Bam HI and analyzed as above. Miniprep DNA from an individual picked clone (pUCDPK) which was sensitive to Asp 718 but resistant to Acc I and Bam HI was used in the above construction of pUCL1.

(3) pUCL2. Ten μg of pUCL1 was digested with restriction endonucleases Asp 718 (20units) and Pst I (20 units) in 25 μl of Asp buffer [6 mM Tris-HCl (pH 8.5), 75 mM NaCl, 6 mM MgCl$_2$, 6 mM 2 mercaptoethanol, 100 μg/ml BSA] for 2 hours at 37° C. This material was diluted to 40 μl, adjusted to contain T4 DNA polymerase buffer [16.6 mM (NH$_4$)$_2$SO$_4$, 67 mM Tris-HCl (pH 8.8), 6.7 mM MgCl$_2$, 10 mM 2 mercaptoethanol, 6.7 mM EDTA, 167 μg/ml BSA], dXTPs (445 molar), and T4 DNA polymerase (4 units) were added, and then the mixture was incubated for 60 minutes at 37° C. The product of this reaction was diluted to 10 μg/ml. 100 μl (1 μg) was adjusted to contain T4 DNA ligase buffer, and T4 DNA ligase (200 units) was added, followed by overnight ligation at 12° C. To the ligated material was added 10 × Asp buffer (12 μl), Pst I (2 units) and Asp 718 (2 units), followed by incubation for 2 hours at 37° C. This material was used to transform E. coli DH5 as above. Individual colonies were picked and screened by digestion with Pst I and Asp 718. The product of these reactions (which was resistant to both Pst I and Asp 718) was plasmid pUCL2. Large-scale pUCL2 plasmid DNA was isolated and used for the construction of pLP.

(4) pLP. Ten μg of pUCL2 was digested with Hin dIII (40 units) and Eco RI (40 units) in Eco RI buffer [50 mM NaCl, 100 mM Tris-HCl (pH 7.5), 5 mM MgCl$_2$, 100 μg/ml BSA] for 2 hours at 37° C. Likewise 10 μg of pcDV [Okayama et al., Mol. Cell. Biol. 3:280 (1983)] was restricted with Hin dIII and Eco RI. These DNAs were purified by electrophoresis and electroelution as above. The purified Hin dIII-Eco RI fragment (9 ng) from pUCL2 was ligated overnight at 12° C. to the Hin dIII-Eco RI fragment (33.5 ng) from pcDV in a 10 μl reaction containing T4 DNA ligase buffer and T4 DNA ligase (80 units). This material was used to transform E. coli DH5. Individual colonies were picked and mini-prep DNAs were screened by digestion with Hin dIII and Eco RI. The product of these reactions contained the Hin dIII-Eco RI fragments from pUCL2 and pcDV and was designated plasmid pLP (FIG. 2).

pLP contains the SV40 origin of DNA replication, the SV40 early region promoter and the SV40 late region intervening sequence separated by a spacer segment from the SV40 late region polyadenylation signal. As such, this plasmid has all the required elements for expression of cloned cDNAs in mammalian cells. This vector also contains the β-lactamase gene and pBR origin derived from pcDV. Within the spacer region the following restriction sites occur: The Sac I, Eco RI and Kpn I. The Sac I site is adjacent and 3' to the intervening sequence, whereas the Kpn I site is adjacent and 5' to the polyadenylation signal.

Oligonucleotide Adaptors

Four oligonucleotides of defined sequence were synthesized:

5'pCCCCGCGGCCGCCCCCCCCCCp 3';  (1)

5'pCGGCCGCGGGGAGCTOH 3';    (2)

5'pCGGGGCGGCCGCT$_{40}$OH 3';    (3)

5'pCGGCCGCCCCGGTACAOH 3';    (4)

Oligonucleotides 2, 3 and 4 were synthesized with 3' and 5' hydroxyl termini, then converted enzymatically by polynucleotide kinase to the 5' phosphorylated form. Their synthesis was carried out on an Applied Biosystems (Foster City, Calif.) 380B DNA synthesizer employing 10 µM scale synthesis, methyl phosphoramidite reagents and the trityl-off cycle. Oligonucleotides 2, 3 and 4 (2 ml each) were deprotected by the addition of concentrated NH$_4$OH (1.7 ml each) followed by incubation for 2 hours at 60° C. in tightly capped tubes. The oligonucleotides were cooled to room temperature, then evaporated to dryness in a speed-vac concentrator (Savant, Farmingdale, N.Y.). The oligonucleotides were washed three times with 200 µl of absolute ethanol, then dried between each wash in the speed-vac. Oligonucleotides were resuspended in 400 µl of doubly distilled water, then 5 A$_{260}$ OD units of each were purified by electrophoresis through a 16% acrylamide gel containing 7M urea. Appropriate bands were identified by UV-shadowing, excised and then the oligonucleotides were eluted from the gel slices by incubation for 24 hours at 37° C. in 4 ml of 0.5M ammonium acetate, 50 mM Tris-HCl (pH 7.5) and 2 mM EDTA. Eluted oligonucleotides were purified on a G-25 column (Pharmacia LKB, Piscataway, N.J.), speed-vac dried, washed three times with ethanol (as above), then resuspended in water. Oligonucleotide 1 was obtained from the Midland Certified Reagent Co., Midland, Tex. It was synthesized with both 5' and 3' phosphate groups. 1.5 nmoles of oligonucleotides 1 and 2 were annealed to each other in a volume of 100 µl by brief (2 minute) boiling following by slow cooling to 25° C. In similar fashion, oligonucleotides 3 and 4 were annealed to each other. The annealing reactions yield two double-stranded oligonucleotide adaptors: pair ½ and pair ¾. Adaptor ½ has at one end a Sac I complementary overhang; the other end has a 3' overhang of 10 deoxycytidylate (dC) residues ending in a terminal 3' phosphate (3'P) group. Adaptor ¾ has at one end a Kpn I complementary overhang; the other end has a 3' overhang of 40 deoxythymidylate (dT) residues ending in a terminal 3' hydroxyl group. The structure of the annealed adaptor pairs is shown in FIG. 3A.

Preparation of Asymmetrically Tailed Linker-Primer

Five hundred micrograms of plasmid pLP was digested to completion with restriction endonucleases Kpn I (2000 units) and Sac I (2000 units) in a volume of 6.0 ml for 4 hours at 37° C. The large fragment of the plasmid was purified by agarose gel electrophoresis followed by electroelution as above. The gel purified Kpn I/Sac I cut pLP DNA (110 µg, 50 pmol) was mixed with a 25-fold molar excess (1.25 nmol) of adapter pairs ½ and ¾ in 650 µl containing T4 DNA ligase buffer and T4 DNA ligase (12,000 units). The mixture was ligated for 16 hours at 12° C. Gel electrophoresis and electroelution as above was used to purify the linear pLP DNA linked to adaptors away from vector multimers and free adaptors. Sequential chromatography with oligo (dA) and oligo (dG) celluloses [essentially as described by Okayama et al., Meth. Enzymol. 154:3 (1987)] was used to recover linker-primer which had been ligated to both the ½ (dT tailed) and ¾ (dC tailed) adaptors. This asymmetrically tailed linker-primer was the starting material for priming cDNA libraries. See FIG. 4 for a diagram of the preparation and structure of the tailed linker-primer.

Construction of pLP-cDNA Libraries pLP-cDNA expression libraries were constructed from the following poly (A)+ mRNAs: 7.5 kb poly (A)+ defined mRNA (BRL, Bethesda, Md.), rat heart and lymphoma 8226 poly (A)+ mRNAs. The heart and lymphoma mRNAs were isolated by the guanadinium isothiocyanate method followed by selection on oligo dT cellulose as described in Maniatis et al. (supra, at pp 88-94). Poly (A)+ mRNA (2 µg) was denatured in 10 µl of deionized water at 65° C. for 3 minutes, chilled on ice, and mixed with 1.0 µg of asymmetrically tailed linker-primer DNA, buffer [10 mM Tris hydrochloride (pH 8.35 at 42° C.), 6 mM MgCl$_2$, 30 mM KCl], 2 mM deoxynucleotide triphosphates, and reverse transcriptase (10 units) in a final volume of 20 µl. First-strand cDNA was synthesized by incubating at 42° C. for 60 minutes; the reaction was terminated by adding 1.0 µl of 0.5M EDTA. The reaction mixture was passed over a Sephadex G-50 spun column (5 prime 3 prime, Paoli, Pa.) to remove unincorporated dXTPs. The recovered sample (20 µl) was extracted with an equal volume of phenol-chloroform. The aqueous phase was adjusted to 0.3M in sodium acetate and precipitated at −70° C. by the addition of 2.5 volumes of ethanol. Then, 10 to 20 deoxyguanylate (dG) residues were added to the first cDNA strand by terminal deoxynucleotidyl transferase. The tailing reaction (20 µl) contained 1.0 µg of pLP vector DNA linked to the first cDNA strand, 140 mM sodium cacodylate—30 mM Tris-HCl (pH 6.8), 1 mM CoCl$_2$, 0.1 mM DTT, 5 µg of poly(A), 2 nmoles of $^3$H dGTP (100 cpm/pmol), and terminal transferase (10 U). The tailing reaction was incubated at 37° C. for 2 minutes. Tail length was determined by TCA precipitation as described by Okayama et al. [Meth. Enzymol. 154:3 (1987)]. Because of the 3'P block on the dC end of the linker-primer, dG residues were only added to the 3' terminus of the the first cDNA strand. The dG tailed RNA-DNA complex was diluted to 2 µg/ml, made 0.1M in NaCl, then self-annealed by sequential treatment at 65° for 5 minutes, 45° C. for 30 minutes, followed by chilling on ice.

The annealed material was cyclized by overnight ligation at 15° C. at a vector concentration of 1 µg/ml in a 1.0 ml reaction containing E. coli DNA ligase (5 µg) and E. coli ligase buffer as described by Okayama et al. [Mol. Cell. Biol. 2:161 (1982)]. The 3'P block was removed by adding calf intestine alkaline phosphatase (8 units) and then incubating the reaction at 37° C. for 30 minutes. The phosphatase was inactivated by treatment at 65° C. for 10 minutes. Replacement of the RNA with second-strand cDNA utilized RNase H (6 units), DNA polymerase I (12 units) and E. coli ligase (2.5 µg) in a 1 ml reaction containing 1 µg of vector DNA, as described by Okayama et al. [Mol. Cell. Biol. 2:161 (1982); Mol. Cell. Biol. 3:280 (1983)]. A portion of the reaction mixture (86 pg of vector) was then used to transform electro-competent E. coli (see below). The libraries selected on ampicillin-containing medium contained 5.1-7.7×10$^4$ independent transformants from 86 pg vector (i.e., 5.9-9×10$^8$ transformants per µg of starting pLP vector).

Transformation of E. coli

Competent *Escherichia coli* strains DH1 and DH5 were obtained from Bethesda Research Laboratories, Bethesda, Md. These cells were used exclusively in the construction of pLP and vector intermediates prior to pLP.

*E. coli* DH5 was made competent by the procedure of Hanahan [Techniques for Transformation of *E. coli*, DNA Cloning, Vol. 1 (Glover, Ed.), 1985, IRL press, pp. 109-135]. Hanahan competent cells yielded $4-7 \times 10^7$ independent bacterial colonies per µg of supercoiled plasmid DNA. These cells were used exclusively in tests summarized below in Table I.

*E. coli* DH5 and WM 1100 (Bio-Rad, Richmond, Calif.) were made electro-competent by the procedure of Dower et al. [Nucleic Acids Res. 13:6127 (1988)]. For small scale electro-transformations, 1 µl of library DNA (860 pg) was diluted 1:10 in water, then 1 µl of the diluted library DNA was mixed on ice with 40 µl of electro-competent *E. coli*. Using a Bio-Rad Gene Pulser apparatus with a pulse controller, current was applied to the cell-DNA mixture in cuvettes (0.2 cm gap). Gene pulser settings were 2500 volts, 960 µF, 400 ohms. Relaxation times varied from 8.8 to 9.2 msec. Large scale electro-transformations were carried out in similar fashion by increasing the volume of cells (360 µl) and the amount of added library DNA (9 µl). Relaxation times varied from 7.0 to 7.2 msec. Electro-competent cells yielded efficiencies of $10^9$ to $10^{10}$ independent bacterial colonies per µg of supercoiled pBR322 plasmid DNA. These electro-competent cells were used exclusively for electro-transformation of the cDNA libraries.

Comparison With Other Cloning Methods

To demonstrate the efficiency of the present method over the methods of the prior art, a comparison study was carried out, the results of which are shown in Table I.

TABLE I
Relative Efficiencies of cDNA Cloning

| Vector | Clones Per µg of Vector | Clones Per µg of cDNA | Clones Per µg of RNA |
|---|---|---|---|
| pLP | $9 \times 10^8$ | $1.8 \times 10^9$ | $4.5 \times 10^8$ |
| pcDV | $6 \times 10^7$ | $1.2 \times 10^8$ | $3 \times 10^7$ |
| pCDM8[a] | $10^6-10^7$ | $1-2 \times 10^6$ | $1 \times 10^6$ |
| λgt11[b] | $1 \times 10^6$ | $2 \times 10^7$ | $1 \times 10^7$ |
| Supercoiled plasmid pBR322 | $0.5-1.0 \times 10^{10}$ | | |
| λDNA[b] | $1-2 \times 10^9$ | | |

[a] Data from Bottger [BioTechniques 6:878 (1988)] and Aruffo et al. [Proc. Natl. Acad. Sci. U.S.A. 84:8573 (1987)]
[b] Data from Huynh et al. [DNA Cloning, A Practical Approach, Vol. 1, IRL Press, Glover ed., 1985, p. 49] and Sorge [Strategies in Molecular Biology 1:3 (1988)]

cDNA libraries were made from poly (A)+ mRNA using the pcDV vector and method of Okayama et al. [Mol. Cell. Biol. 2:161 (1982); Mol. Cell. Biol. 3:280 (1983); Meth. Enzymol. 154:3 (1987)] and the modified pLP vector and method of this invention. Using the Okayama et al. method and electro-competent *E. coli* $6 \times 10^7$ independent bacterial transformants per microgram of tailed pcDV vector were obtained. This is a 60-fold improvement in complexity over previously published reports with the pcDV vector. This improvement reflects the high efficiency of electro-transformation of *E. coli*. Using the modified pLP vector, electro-competent *E. coli* and the method of this invention, however, $9 \times 10^8$ independent bacterial transformants per microgram of tailed pLP vector were obtained.

This is a 15-fold improvement in complexity (i.e., the total number of independent clones) over the results with pcDV. The complexity of libraries made by the method of this invention typically ranges from about 6 to about 20 percent of the theoretical maximum (i.e., the transformation efficiency of supercoiled plasmid DNA).

Table I shows that the efficiency (based upon total complexity) of the present method is 45 to 900-fold greater than existing published methods for generating cDNA libraries. Modified pLP libraries are about 45-fold more efficient than λgt11 libraries based upon clones per microgram starting RNA (Table I). However, pLP libraries are 90 to 900-fold more efficient than published plasmid-based library procedures.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. An asymmetrically tailed plasmid primer comprising a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group.

2. The asymmetrically tailed plasmid primer of claim 1 in which the oligo (dT) extension contains from about 10 to about 200 nucleotide residues and the oligo (dC) or oligo (dG) extension contains from about 8 to about 25 nucleotide residues.

3. The asymmetrically tailed plasmid primer of claim 2 in which the oligo (dT) extension contains from about 40 to about 60 nucleotide residues and the oligo (dC) or oligo dG) extension contains from about 10 to about 12 nucleotide residues.

4. The asymmetrically tailed plasmid primer of claim 3 which has been produced by Sac I and Kpn I cleavage of plasmid pLP, wherein each termini produced by the cleavage is joined to the complementary adaptor of FIG. 3A.

5. The asymmetrically tailed plasmid primer of claim 3 which has been produced by Eco RI and Hin dIII cleavage of plasmid pUC19, wherein each termini produced by the cleavage is joined to the complementary adaptor of FIG. 3B.

6. A method for cloning cDNA, comprising:
 (a) treating an mRNA preparation with an asymmetrically tailed plasmid primer comprising a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group, under conditions in which polyadenylate tails in the mRNA specifically anneal to the oligo (dT) extension of the primer to form a primer:mRNA complex;
 (b) treating the primer:mRNA complex under conditions in which a first cDNA strand is synthesized using the annealed mRNA as a template, thereby forming a primer-linked cDNA:mRNA duplex;

(c) adding an oligo (dG) or oligo (dC) extension to the 3' end of the first cDNA strand, which extension is complementary to the phosphate-terminated extension of the primer; and (d) treating the cDNA:mRNA duplex of step (c) under conditions in which a second cDNA strand is synthesized, using the first cDNA strand as a template.

7. The method of claim 6 in which a closed circular plasmid is produced.

8. The method of claim 7 in which a closed circular plasmid is introduced into a unicellular host organism, and the host organism is cultured under conditions in which the plasmid is replicated.

9. The method of claim 8 which comprises:

a) treating a mRNA preparation with an asymmetrically tailed plasmid primer comprising a cut, double-stranded DNA plasmid containing a functional origin of replication and at least one functional selection marker gene, one 3' terminus of which contains an oligo (dT) extension, the other 3' terminus of which contains an oligo (dC) or oligo (dG) extension terminated by a 3' phosphate group, under conditions in which polyadenylate tails in the mRNA specifically anneal to the oligo (dT) extension of the primer to form a primer:mRNA complex;

(b) treating the primer:mRNA complex under conditions in which a first cDNA strand is synthesized using the annealed mRNA as a template, thereby forming a primer-linked cDNA:mRNA duplex;

(c) adding an oligo (dG) or oligo (dC) extension to the 3' end of the first cDNA strand, which extension is complementary to the phosphate-terminated extension of the primer;

(d) annealing the oligo (dG) or oligo (dC) extension of the first cDNA strand to the phosphate-terminated extension of the primer;

(e) ligating the 3' terminus of the oligo (dG) or oligo (dC) extension to the 5' end of the primer;

(f) removing the 3' phosphate group from the phosphate-terminated extension of the primer;

(g) digesting the mRNA in the cDNA:mRNA duplex;

(h) synthesizing a second cDNA strand using the first strand as a template;

(i) ligating the second cDNA strand to the plasmid to form a closed circular plasmid;

(j) introducing the closed circular plasmid into a unicellular host organism; and (k) culturing the host organism under conditions in which the plasmid is replicated.

10. The method of claim 9 in which the oligo (dT) extension of the primer contains from about 10 to about 200 nucleotide residues and the oligo (dC) or oligo (dG) extension of the primer contains from about 8 to about 25 nucleotide residues.

11. The method of claim 10 in which the oligo (dT) extension of the primer contains from about 40 to about 60 nucleotide residues and the oligo (dC) or oligo (dG) extension of the primer contains from about 10 to about 12 nucleotide residues.

12. The method of claim 11 in which the host organism is an E. coli bacterium.

13. The method of claim 12 in which the asymmetrically tailed plasmid primer has been produced by Sac I and Kpn I cleavage of plasmid pLP, wherein each termini produced by the cleavage is joined to the complementary adaptor of FIG. 3A.

14. The method of claim 12 in which the asymmetrically tailed plasmid primer has been produced by Eco RI and Hin dIII cleavage of plasmid pUC19, wherein each termini produced by the cleavage of joined to the complementary adaptor of FIG. 3B.

15. The method of claim 12 in which the first cDNA strand is synthesized using reverse transcriptase, the oligo (dG) or oligo (dC) extension is added to the first cDNA strand using terminal deoxynucleotidyl transferase, the ligation steps are carried out using E. coli or T4 DNA ligase, the phosphate group is removed using alkaline phosphatase, the mRNA is digested using RNase H, and the second cDNA strand is synthesized using an enzyme having the activities of DNA polymerase I.

16. The method of claim 15 in which the closed circular plasmid is introduced into the bacterium by electrotransformation.

17. A kit for carrying out the cloning of mRNA, comprising one bottle each of solutions of the following reagents in quantities sufficient to carry out multiple clonings:

(a) an asymmetrically tailed plasmid primer of claim 1, (b) a DNA ligase, (c) a terminal deoxynucleotidyl transferase, (d) a reverse transcriptase, (e) a DNA polymerase, (f) a ribonuclease, (g) an alkaline phosphatase, and (h) a host unicellular organism.

18. The kit of claim 17 in which the asymmetrically tailed plasmid primer has been produced by Sac I and Kpn I cleavage of plasmid pLP and contains the adaptors of FIG. 3A.

19. The kit of claim 17 in which the asymmetrically tailed plasmid primer has been produced by Eco RI and Hin dIII cleavage of plasmid pUC19 and contains the adaptors of FIG. 3B.

20. The kit of claim 17 in which the DNA ligase is E. coli or T4 DNA ligase, the reverse transcriptase is Moloney murine leukemia virus or avian myeloblastosis virus reverse transcriptase, the DNA polymerase has the activities of DNA polymerase I, and the ribonuclease is RNase H.

* * * * *